United States Patent [19]

Butti et al.

[11] 3,985,871

[45] Oct. 12, 1976

[54] PHARMACEUTICAL HEPARINOIDIC FACTOR-CONTAINING COMPOSITION AND THERAPEUTIC USE THEREOF

[75] Inventors: Adriano Butti, Como; Giuseppe Prino, Milan; Marisa Mantovani, Como, all of Italy

[73] Assignee: Crinos Industria Farmacobiologica S.p.A., Como, Italy

[22] Filed: Mar. 26, 1975

[21] Appl. No.: 562,216

[30] Foreign Application Priority Data

Apr. 4, 1974 Italy.................................. 50134/74

[52] U.S. Cl................................. 424/104; 424/95; 424/183
[51] Int. Cl.² ................. A61K 31/725; A61K 35/38
[58] Field of Search...................... 424/95, 183, 104

[56] References Cited

UNITED STATES PATENTS

| | | | |
|---|---|---|---|
| 2,661,315 | 12/1953 | Jurist et al. .......................... | 424/183 |
| 3,000,787 | 9/1961 | Bianchini............................ | 424/101 |
| 3,574,831 | 4/1971 | Engel et al.......................... | 424/183 |

*Primary Examiner*—Sam Rosen
*Attorney, Agent, or Firm*—Browdy and Neimark

[57] ABSTRACT

A pharmaceutical composition comprising an anhydrous suspension of a heparinoidic factor in a suspending medium selected from vegetable and animal fats, aliphatic acids and their alkyl esters, in the presence of an anionic dispersant (typically sodium taurocholate), is orally administrable to patients in need of a medicine having antiplasmin inhibiting effect.

5 Claims, No Drawings

PHARMACEUTICAL HEPARINOIDIC FACTOR-CONTAINING COMPOSITION AND THERAPEUTIC USE THEREOF

BACKGROUND OF THE INVENTION

1. Field of the Invention

This invention relates to a novel orally administrable therapeutic composition having an antiplasmin inhibiting effect. More particularly, this invention relates to a novel composition comprising an anhydrous suspension of a heparinoidic factor and to the therapeutic use thereof.

2. Description of the Prior Art

Heparinoidic factors have long since come into general use as advantageous substitutes for heparin in the prophylaxis and therapy of atherosclerotic disease. In fact, though heparin is highly effective in normalizing the lipoproteinemic condition and the relation between alpha- and beta-globulins, it is well known that heparin also shows a lasting anti-coagulant action. Consequently, any prolonged treatment with this drug calls for a continuing and careful detection of the coagulation time with a view to preventing hemorrhage. It is also known that heparin cannot be satisfactorily administered either by the intramuscular route in view of the large hematoma produced at the site of the injection, or by the oral route because of instability brought about by digestive enzymes.

In the U.S. Pat. No. 3,000,787 issued to the same assignee as the present application and herein incorporated by reference, a heparinoid anti-cholesterolemic factor referred to as ATEROID was disclosed. ATEROID, which is in some aspects similar to heparin, has essentially no anti-coagulant effect at the therapeutic levels of administration per the treatment discussed hereinabove.

The aforementioned patent discloses that ATEROID can be extracted from the small intestine and particularly from the duodenum of mammals, by means of methods suitable for the isolation of aminopolysaccharidic or glycoproteic compounds. The heparinoidic factor disclosed in U.S. Pat. No. 3,000,787, for the purpose of the present specification and claims, will hereinafter be referred to as HPF-1.

Also in the U.S. Pat. No. 3,181,996 issued to the same assignee as the present application and also incorporated herein by reference, there has been disclosed a method of obtaining a heparinoidic factor of pancreatic origin. This heparinoidic factor, for the purpose of the present specification and claims, will hereinafter be referred to as HPF-2.

It is also known that plasmin is the fibrinolytic enzyme that dissolves the fibrin of blood clots obstructing normal hematic flow. An increase of plasmin inhibitors has been reported in a number of patients suffering from arterial hypertension of atherosclerotic etiology, ischemia or acute myocardial infarction, angina and cerebral thrombosis (see J. Prokopowicz et al. *Thrombos. Diathesihaemorrh.* 1967, 17, 1 and G. Tsitouris et al., *J.Atheroscl. Res.* 1967, 7, 425).

While it is known that orally administered heparin is inactive both on lipid metabolism and coagulation (see British Pat. No. 1,135,783; 1,135,784; 1,157,754; and U.S. Pat. Nos. 3,546,338 and 3,574,831), the foregoing heparin oidic factors are active on the lipid metabolism when orally administered. However, the oral administration of these factors is ineffective to decrease the level of the plasmin inhibitors. In fact, in order to decrease the level of the plasmin inhibitors by means of heparinoidic factors, it is necessary to administer them to rats by the intraperitoneal route (see Prino and Mantovani, *Minerva Medica*, 60, 1969, 5015–5022).

Parenteral administration of drugs is usually regarded as being undesirable because it is troublesome, time-consuming and painful to the patient. Furthermore, it requires trained personnel and carefully controlled sterile conditions at the site of administration. Consequently, it is obviously preferred to administer oral medicinal compositions, whenever the same therapeutic effect as that shown by the parenterally administered drug, can be obtained. On the other hand, the desirability to maintain a normal antiplasmin level in patients suffering from the foregoing diseases is apparent. There is therefore an actual need for a therapeutic composition that is orally administrable to patients in need of an antiplasmin inhibiting composition.

SUMMARY OF THE INVENTION

We have now found a noval heparinoid-containing pharmaceutical composition, which is active in inhibiting antiplasmin agents and is orally administrable.

The orally administrable pharmaceutical composition having an antiplasmin inhibiting effect according to our invention comprises an anhydrous suspension of a heparinoidic factor in a suspending medium selected from the group consisting of vegetable and animal fats, saturated and unsaturated aliphatic acids, their alkyl esters and mixtures thereof, in the presence of at least 0.1 parts by weight, based on the heparinoidic factor of a dispersant.

DESCRIPTION OF THE PREFERRED EMBODIMENTS

As aforementioned the composition in accordance with our invention is anhydrous. We have in fact, found that water is not a critical component of the composition, because its exclusion does not quantitatively affect the antiplasmin inhibiting action of the heparinoidic factors. On the other hand the advantage of having at one's disposal an anhydrous composition instead of a similar water-containing composition is apparent because the technological difficulties of producing aqueous solution-containing enterisoluble capsules are well known.

We have also surprisingly found that while the heparinoidic factors are not active as antiplasmin inhibitors when orally administered in addition to a dispersant only (e.g. sodium taurocholate), they become orally active when suspended, along with the dispersant, in a suspending medium as above defined.

The preferred heparinoidic factors of the compositions of the present invention are HPF-1 (ATEROID - disclosed in U.S. Pat. No. 3,000,787) and HPF-2 (the heparinoidic factor obtainable by the method disclosed in the previously cited U.S. Pat. No. 3,181,996).

The dispersant of the heparinoidic factor is preferably an anionic dispersant. Suitable anionic dispersants are: sodium taurocholate, sodium glycolate, sodium cholate, sodium lauryl sulfate, dioctyl sodium sulfosuccinate, alkyl aryl sulfate (G-3300 Atlas Powder Co.), fatty acid-saccharose esters, polyoxyethylene sorbitan monolaurate, mannite monooleate and polysorbate 20 (Tween 20). Among the anionic dispersants, sodium taurocholate and sodium laurysulfate are particularly preferred. The amount of the dispersant preferably ranges between about 0.2 and 0.5 parts by weight per part of heparinoidic factor, although amounts as low as 0.1, or as high as 0.8 parts by weight per part of heparinoidic factor, can be effectively used.

As aforementioned, the suspending medium comprises vegetable and animal fats, saturated and unsaturated aliphatic acids, having from 4 to 20 carbon atoms, their alkyl (preferably ethyl) esters and mixtures thereof.

Among the vegetable and animal fats, olive oil, peanut oil, coconut oil, corn oil, tributyrin and commercial-grade axunge, are preferred.

Among the aliphatic acids, arachidonic acid, linoleic acid, linolenic acid, oleic acid, octanoic acid, are preferred, along with the alkyl (preferably ethyl) esters thereof.

The compositions of this invention have to be coated with an enteric coating in order to prevent degradation of the heparinoidic factor by gastric juice. Non-limiting examples of enteric coatings are cellulose acetate, phthalates and styrene-maleic anhydride copolymers. Other suitable compounds useful as enteric coatings will be readily apparent to those skilled in this art.

The following example illustrates the present invention and is not intended to limit the scope thereof.

EXAMPLE

This example shows the antiplasmin inhibiting action of a composition according to this invention.

A heparinoidic factor, HPF-1, was extracted from mammalian duodenum and thereafter purified, following the procedures disclosed in the U.S. Pat. No. 3,000,787.

HPF-1 was thoroughly dispersed with sodium taurocholate and suspended in a 8:2 (by volume) coconut oil/corn oil mixture. The final composition was as follows:

| | |
|---|---|
| HPF-1 | 300 mg |
| Sodium taurocholate (Na T) | 60 mg |
| Coconut oil/corn oil (C.C.O.) balance to | 10 ml. |

A number of rats was treated according to the procedure disclosed by Engel and Fahrenbach in *Proc. Soc. Exptl. Biol. Med.* 1968, 129, 772, which is incorporated herein by reference.

Antiplasmin level in rats was experimentally increased by means of TRITON and evaluated according to the procedure disclosed by Prino and Mantovani in Coagulation, 1970, 3, n.3, 273–278; which is incorporated herein by reference.

The data are summarized in the following table:

TABLE

Effect on antiplasmin level experimentally increased by means of TRITON, of intraduodenal administration to rats of heparinoidic factor (300 mg/kg of body weight) suspended in a mixture of coconut and corn oil, in the presence of sodium taurocholate, in comparison with the effect caused by administration of saline, sodium taurocholate + coconut oil/corn oil and heparinoidic factor, respectively

| Group (1) | Treatment (2) | Antiplasmin units | % | P (3) vs group 2 |
|---|---|---|---|---|
| 1 | Saline (intraduodenally) | 145.9±3.3 | 100 | 0.001 |
| 2 | NaT + C.C.O. (intraduodenally) | 298.6+10.5 | 204.7 | — |
| 3 | HPF$^{-1}$aq.solution (orally) | 285.7±9.4 | 196.0 | N.S.(4) |
| 4 | HPF$^{-1}$+ NaT +C.C.O. (5) | 188.9±7.1 | 129.5 | 0.001 |

Note:
(1) Each group contained 50 rats.
(2) All rats, except those in group 1, were previously intravenously administered with TRITON R according to the above mentioned procedure of Prino And Mantovani.
(3) P means probability.
(4) N.S. means not statistically significant.
(5) The composition in accordance with this invention, HPF$^{-1}$+NaT+C.C.O., was administered to group 1 rats by intraduodenal intubation at a dosage of 300 mg/kg of body weight (1 ml/100mg body weight).

The foregoing data clearly show that the antiplasmin level, after having been experimentally increased, can be brought back to its normal value by means of intraduodenal administration of the anhydrous compositions of this invention.

It should be understood that the effectiveness on animals shown hereinabove is acceptable evidence in this art of effectiveness on humans due to the correlation of these tests on standard test animals with human utility. In fact, the antiplasmin inhibiting effect has been studied also on humans, according to the experimental test disclosed by G. Tsitouris et al. in the Journal of Atherosclerosis Research. These studies have been carried out on patients suffering from cerebral thrombosis and ischemic cardiopathy, evidencing a strong antiplasmin inhibiting activity with both the above mentioned heparinoidic factors. Furthermore, while only two heparinoidic factors have been specifically disclosed, it should be understood that the effectiveness of the combination of ingredients of the present composition would be expected for any heparinoidic factor.

It will be obvious to those skilled in the art that various changes may be made without departing from the scope of the invention and the invention is not to be considered limited to what is described in the specification.

What we claim is:
1. An orally administrable therapeutic composition producing an antiplasmin inhibiting effect, comprising an anhydrous suspension of:
   1. an effective amount to inhibit antiplasmin of a heparinoidic factor in
   2. a suspending medium consisting of vegetable and animal fats selected from the group consisting of olive oil, peanut oil, coconut oil, corn oil, tributyrin and commercial grade axunge,
saturated and unsaturated aliphatic acids selected from the group consisting of arachidonic acid, linoleic acid, linolenic acid, oleic acid, actanoic acid, and alkyl esters thereof, or
mixtures thereof, in the presence of
3. at least 0.1 parts by weight based on the heparinoidic factor of an anionic dispersant selected from the group consisting of sodium taurocholate, sodium glycolate, sodium cholate, sodium laurylsulfate, dioctyl sodium sulfosuccinate, alkyl aryl sulfate, fatty acid-saccharose esters, polyoxyethylene sorbitan monolaurate, mannite monooleate, and polysorbate 20.

2. The composition of claim 1, wherein the heparinoidic factor is selected from the group consisting of HPF-1 and HPF-2.

3. The composition of claim 1 in unit dosage form.

4. A therapeutic method of treating a patient in need of an antiplasmin inhibiting composition, which comprises orally administering to said patient an antiplasmin inhibiting effective amount of the composition of claim 1.

5. The composition of claim 1 wherein said anionic dispersant is present in amounts between about 0.2 and about 0.5 parts by weight per part of heparinoidic factor.

* * * * *